United States Patent
Coleman et al.

(10) Patent No.: US 6,547,731 B1
(45) Date of Patent: Apr. 15, 2003

(54) METHOD FOR ASSESSING BLOOD FLOW AND APPARATUS THEREOF

(75) Inventors: D. Jackson Coleman, Haworth, NJ (US); Katherine W. Ferrara; Dustin E. Kruse, both of Charlottesville, VA (US); Ronald H. Silverman, Brooklyn, NY (US)

(73) Assignees: Cornell Research Foundation, Inc., Ithaca, NY (US); University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 09/305,593

(22) Filed: May 5, 1999

Related U.S. Application Data
(60) Provisional application No. 60/084,263, filed on May 5, 1998.

(51) Int. Cl.[7] .................................................. A61B 8/02
(52) U.S. Cl. ...................................................... 600/437
(58) Field of Search ................................ 600/453–456; 73/861, 25–27

(56) References Cited

U.S. PATENT DOCUMENTS

| | | | |
|---|---|---|---|
| 3,881,466 A | * 5/1975 | Wilcox ........................ | 73/626 |
| 4,070,905 A | * 1/1978 | Kossoff ....................... | 73/614 |
| 4,265,126 A | * 5/1981 | Papadofrangakis al. ..... | 600/441 |
| 4,276,491 A | * 6/1981 | Daniel ........................ | 310/335 |
| 4,319,489 A | * 3/1982 | Yamaguchi et al. .......... | 73/626 |
| 4,893,283 A | * 1/1990 | Pesque ........................ | 367/7 |
| 5,105,814 A | * 4/1992 | Drukarey et al. ............ | 600/443 |
| 5,409,010 A |   4/1995 | Beach et al. | |
| 5,664,575 A |   9/1997 | Banjanin et al. | |
| 5,910,119 A | * 6/1999 | Lin ............................ | 600/455 |

FOREIGN PATENT DOCUMENTS

| | | |
|---|---|---|
| EP | 0 016 399 A | 10/1980 |
| EP | 0 628 285 | 12/1994 |
| WO | WO 91/16000 | 10/1991 |

OTHER PUBLICATIONS

Stewart, et al., "Surgical vs Medical Management of Chronic Open–Angle Glaucomo," *American Journal of Ophthalmology*, 122:767–774 (1996).

National Advisory Eye Council, *Vision Research–A National Plan 1999–2003, Executive Summary*, Bethesda, MD; National Institutes of Health, NIII, Pub. No. 98–4288, 18 pages, (1998).

(List continued on next page.)

*Primary Examiner*—Francis J. Jaworski
(74) *Attorney, Agent, or Firm*—Nixon Peabody LLP

(57) ABSTRACT

A method for assessing blood flow in a tissue involving directing a beam through the tissue along overlapping lines of sight and then generating the blood flow data from where the ultrasonic beams overlap to evaluate blood flow in the tissue. More specifically, spatially overlapping beams are generated at a fixed temporal intervals. Spatial overlap allows the spatial distance between overlapping lines-of-sight to be ignored, while moving reflectors within any overlapping line-of-sight will cause detectable changes in range of the moving reflector from one line-of-sight to the next. The rate of motion is determined from the measured change in range and the known time interval between vectors. Processing of data includes alignment of data between lines-of-sight to suppress artifactual motion and a wall filter for isolation of flow-data from stationary structures. An apparatus for assessing blood flow includes a transmission system and a storage system. The transmission system generates a beam which is sequentially transmitted towards the tissue along a plurality of overlapping lines of sight and receives echo data from the transmission along each of the lines of sight. The storage system stores the echo data.

47 Claims, 8 Drawing Sheets

(6 of 8 Drawing Sheet(s) Filed in Color)

OTHER PUBLICATIONS

Ferrara et al., "A New Wideband Spread Target Maximum Likelihood Estimator for Blood Velocity Estimation–Part I: Theory," *IEEE Trans Ultra Ferro Freq Cons.*, 38:1–16 (1991).

Kasai et al., "Real–Time Two–Dimensional Blood Flow Imaging Using an Autocorrelation Technique," *IEEE Transactions On Sonics and Ultrasonics*, SU–32; 458–464 (1985).

Stith et al., "3D Ultrasonic Mapping of the Microvasculature," *IEEE Ultrasonics Symposium*, 1473–6 (1996).

Van Buskirk et al., "Ciliary Vasoconstruction After Topical Adrenergic Drugs," *American Journal of Ophthalmology*, 109:511–7 (1990).

Coleman et al., "Ophthalmic Ultrasonography," *Ultrasonography of Small Parts*, 30:1105–14 (1992).

Zagar et al., "Ultrasonic Mapping of the Microvasculature: Signal Alignment," *Ultrasound in Med. & Biol.*, 24:809–24 (1998).

Stewart et al., "Surgical vs Medical Management of Chronic Open–Angle Glaucomo," *American Journal of Ophthalmology*, 122:767–74 (1996).

Pavlin et al., "High–Frequency Doppler Ultrasound Examination of Blood Flow in the Anterior Segment of the Eye," *American Journal of Ophthalmology*, 126:597–600 (1998).

Pavlin, "Practical Application of Ultrasound Biomicroscopy," *Can J. Ophthalmology*, 30:225–9 (1995).

Williamson et al., "Ocular Blood Flow Measurement," *Perspective*, 939–45.

Vinger, "Sports Eye Injuries A Preventable Disease," *American Academy of Ophthalmology*, 88:108–13 (1981).

Napier et al., "Eye Injuries in Athletics and Recreation," *Survey of Ophthalmology*, 41:229–44 (1996).

Harris et al., "Assessment of Human Ocular Hemodynamics," *Survey of Ophthalmology*, 42:509–33 (1998).

Pavlin et al., "Clinical Use of Ultrasound Biomicroscopy," *American Academy of Ophthalmology*, 98:287–25 (1991).

Whittaker Ferrara et al., "Estimation of Blood Velocity with High Frequency Ultrasound," *IEEE Transactions on Ultrasonics, Ferroelectrics, and Frequency Control*, 43:149–57 (1996).

Williamson et al., "Color Doppler Ultrasound Imaging of the Eye and Orbit," *Survey of Ophthalmology*, 40:255–67 (1996).

Kremkau, F. W. Diagnostic Ultrasound, Principles and Instruments, Fourth Edition, W. B. Saunders Company, Philadelphia (1993).

Leidig, E. and Grunert, D., Pädiatrische Ultraschalldiagnostik und Duplex–Sonographie, Teil II: Physikalische und technische Grundlagen der Ultraschalldiagnostik, Econmed Verlag, Landsberg am Lech (1991).

* cited by examiner

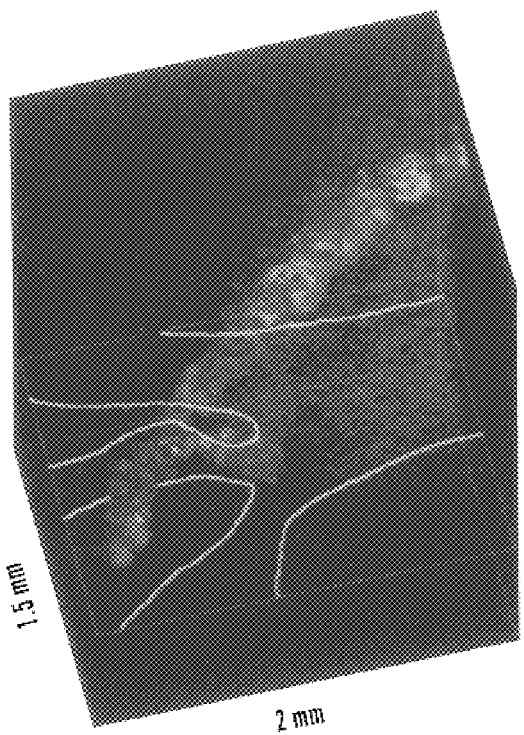 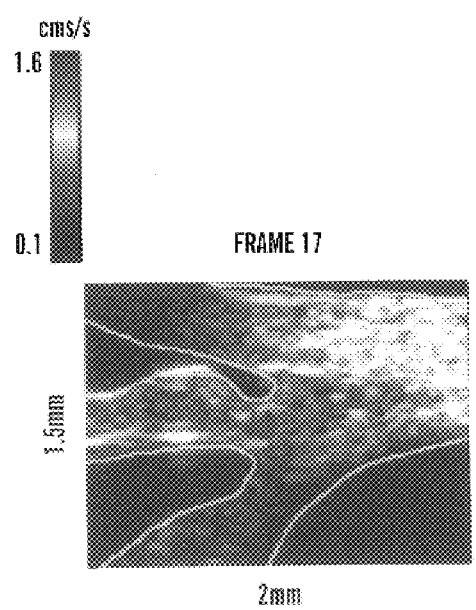
*FIG. 7A*  *FIG. 7B*

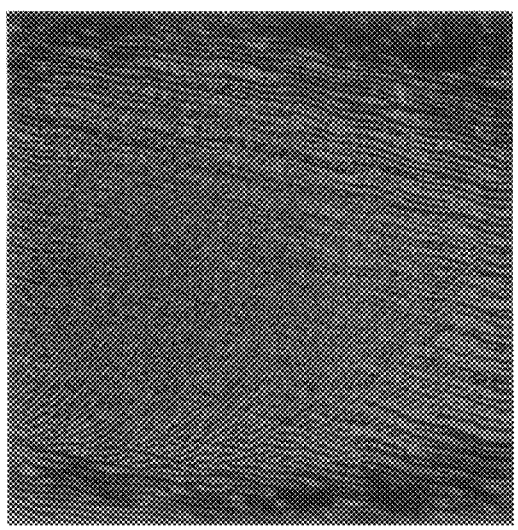
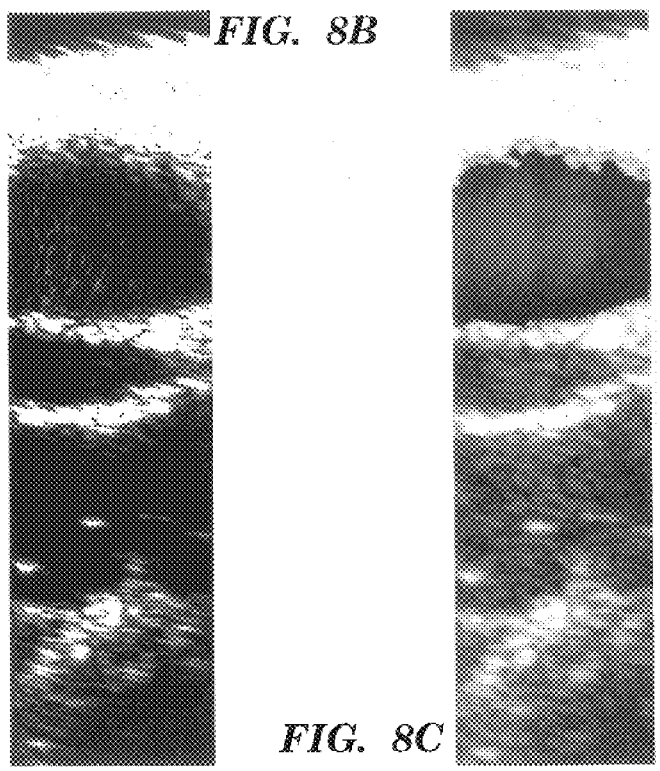
FIG. 8A
FIG. 8B
FIG. 8C

METHOD FOR ASSESSING BLOOD FLOW AND APPARATUS THEREOF

This application is a provisional application of No. 60/084,263 filed May 5, 1998.

This invention was developed with government funding under National Institutes of Health Grant No. R01 EY 11468. The U.S. Government may have certain rights.

FIELD OF THE INVENTION

This invention relates to techniques for assessing blood flow and, more particularly, to a method and apparatus for assessing perfusion and blood velocity in small vessels, such as those in the anterior segment of the eye.

BACKGROUND OF THE INVENTION

The ability to image and quantify blood-flow is crucial in a wide range of medical specialties. Most of the ultrasound units used in radiology departments include the capability of performing color-flow Doppler imaging for this purpose. Depictions of color-flow produced by such conventional Doppler systems must inherently have poorer resolution than the gray-scale ultrasound image of stationary tissues over which the color-flow information is superimposed. The relatively poor resolution of Doppler color-flow limits the size and rate of flow detectable by such systems.

For example, understanding of the mechanisms of ophthalmic diseases including glaucoma and age-related macular degeneration as well as the mechanisms and effectiveness of treatment options has been limited by the lack of appropriate tools and techniques. The clinical significance of an improvement in the management of ophthalmic diseases alone is enormous since about three million people in the United States alone suffer from glaucoma, about one-hundred-thousand per year suffer some form of ocular trauma, and more than six million people in the United States suffer from degenerative retinal diseases. For example, while therapies for glaucoma have been developed, two years after the start of treatment, fifty-six percent of eyes treated first with laser and seventy percent of eyes treated first with medication needed new or extra medications to control pressure within the eye. The lack of appropriate tools and techniques has made it difficult to assess the efficacy of these treatment techniques.

High frequency ultrasound has shown promise for use as a clinical tool and technique, however practical limitations have restricted its use. For example, flow can be detected using a non-Doppler (time-domain) method known as an M-scan. An M-scan consists of a series of vectors acquired at fixed time intervals along one line of sight. In an M-scan, fixed tissue interfaces remain the same distance from the (stationary) transducer (a transducer is a device that emits an acoustic pulse in response to a voltage transient and converts echoes into electrical signals). But if a scatterer (a scatterer is capable of reflecting or scattering ultrasonic energy having an acoustic impedance (density x speed-of-sound) different from the surrounding medium), such as a blood cell conglomeration, is in motion along the line of sight, its range will change with time. One example of a time-domain technique for mapping flow based on acquisition of a series of spatially offset M-scans is disclosed in Ferrara, K. W., et al., "Estimation of Blood Velocity With High Frequency Ultrasound," *IEEE Trans Ultra Freq Cons.*, 43:149–157 (1996) which is herein incorporated by reference. By combining a series of M-scan determinations at independent adjacent spatial positions which are spaced at distances greater than the lateral resolution of the ultrasound beam as shown in FIG. 1A, B-mode images with flow information can be produced. At each spatial position, groups of moving blood cells are detected and their range determined in successive vectors, from which their velocity is computed. When the data are acquired, two-dimensional ("2-D") matrix and three-dimensional (3-D) flow maps can be produced using techniques, such as the one disclosed in Stith, A., et al., "3-D Ultrasonic Mapping of the Microvasculature," *Proc IEEE Ultrason Symp.*, 1473–1476 (1996) which is herein incorporated by reference.

A significant factor limiting the clinical utility of this technique arises from the intermittent nature of the scanning procedure. To scan a diagnostically useful lateral range, M-scan sequences must be acquired at approximately one-hundred spatially independent positions. For each of these positions, transducer motion must be initiated, motion stop confirmed, and data acquired and stored. These operations are time consuming, easily approaching 0.5 seconds per position and expending as much as one minute for a single plane. In the case of the eye, particularly, voluntary and involuntary motions over such a long period are inevitable.

Previous attempts to measure blood flow within the eye using conventional color Doppler ultrasound methods have also been limited by insensitivity to very slow velocities (<1.5 cm/s) as disclosed in T. H. Williamson and A. Harris, "Color Doppler ultrasound imaging of the eye and orbit," *Survey of Ophthalmology*, vol. 40, pp. 255–267, 1996 which is herein incorporated by reference and the inability to resolve vessels smaller than 300 microns. Studies have demonstrated the ability to assess blood flow in the ophthalmic artery and vein and in the short posterior ciliary artery, however these vessels are generally larger and contain higher flow velocities compared to those found in the anterior segment as disclosed in A. Harris, L. Kagemann, and G. A. Cioffi, "Assessment of human ocular hemodynamics." *Survey of Ophthalmology*, vol. 42, pp. 509–533, 1998 and T. H. Williamson and A. Harris, "Ocular blood flow measurement." *British Journal of Ophthalmology*, vol. 78, pp. 939–945, 1994 which are herein incorporated by reference. While studies using high frequency ultrasound demonstrate the ability to resolve structures down to forty microns in the anterior segment of the eye as disclosed in C. J. Pavlin, D. A. Christopher, P. N. Burns, and F. S. Foster, "High-frequency Doppler ultrasound examination of blood-flow in the anterior segment of the eye." *American Journal of Ophthalmology*, vol. 126, pp. 597–600, 1998, and such B-scans of the eye are clinically useful in diagnosing diseases, such as melanoma of the ciliary body and open angle glaucoma as disclosed in C. J. Pavlin, "Practical application of ultrasound biomicroscopy." *Canadian Journal of Ophthalmology*, vol. 30, pp. 225–229, 1995, K. J. Coleman, S. Woods, M. J. Rondeau, and R. H. Silverman, "Ophthalmic ultrasonography." *Radiologic Clinics Of North America*, vol. 30, pp. 1105–1114, 1992, and C. J. Pavlin, K. Harsiewicz, M. D. Sherar, and F. S. Foster, "Clinical use of ultrasound biomicroscopy." *Ophthalmology*, vol. 98, pp. 287–295, 1991 which are herein incorporated by reference, these studies have difficulties with clutter discrimination, resolution, and possibly energy levels.

SUMMARY OF THE INVENTION

A method of assessing blood flow in a tissue in accordance with one embodiment of the present invention includes sequentially directing a beam through the tissue along overlapping lines of sight and then generating blood flow data from echo data from where the beams overlap to evaluate the blood flow in the tissue.

A method of measuring blood flow velocity in at least one vessel in a tissue in accordance with another embodiment of the present invention includes a few steps. First, a beam is sequentially directed through the vessel in the tissue along overlapping lines of sight. Next, blood flow data are generated from echo data from where the beams overlap. Finally, the blood flow velocity in the vessel is determined based on the generated blood flow data.

A method of analyzing a vessel in a tissue in accordance with another embodiment of the present invention includes a few steps. First, a beam is sequentially directed through the vessel in the tissue along overlapping lines of sight. Next, blood flow data are generated from echo data from where the beams overlap. Finally, an image of the vessel is provided based on the generated blood flow data.

An apparatus for assessing blood flow in accordance with one embodiment of the present invention includes a transmission system and a storage system. The transmission system generates a beam which is sequentially transmitted towards the tissue along a plurality of overlapping lines of sight and receives echo data from the transmission along each of the lines of sight. The storage system stores the echo data from the transmission system for each of the lines of sight.

In contrast to prior systems in which an ultrasonic pulse was repeatedly directed to a discrete line-of-sight, the present invention continuously scans over a region in order to rapidly assess blood velocities in blood vessels. Using this invention, a transducer can rapidly translate a beam across a region of interest in an overlapping pattern and sensitive maps of blood velocity in blood vessels can be constructed. As a result, this invention provides an effective and quick, typically less than two seconds, method and apparatus for visualizing and measuring blood flow in a variety of different regions of the body, including vessels smaller than 300 microns and at blood velocities less than 1.5 cm/sec.

One particularly important application of this new mode is in the evaluation of the functionality of the iris, ciliary body and ciliary processes which are located in the anterior segment of the eye. These structures are highly vascular, and share a common blood supply. The iris is a muscular structure, pigmented anteriorly, which controls the aperture size of the pupil, and thus the amount of light focused onto the retina. The ciliary body is a muscular structure in the anterior portion of the eye, responsible for accommodation, and the ciliary processes, which extend off of the ciliary body, produce aqueous fluid. Because these are opaque tissues, they have been inaccessible to prior optical methods, and with vessels smaller than 300 microns, they have been inaccessible to prior color flow mapping systems. With the invention, a 2-D scan of the eye can be obtained in an interval on the order of about one second, and blood flow through the iris and ciliary body can be detected in vessels down to at least forty microns. Assessing blood flow in small vessels that supply structures in the anterior segment, such as in the long posterior ciliary artery or the major arterial circle, and evaluating the response to disease mechanisms and therapeutic interventions is now possible with this invention and is an important step in determining the health of the eye.

Yet another advantage of this invention over prior techniques is that a filter can be applied continuously to the return of the ultrasonic beam or pulse from all regions. As a result, the transient response that occurs along each line-of-sight in traditional Doppler systems can be eliminated.

BRIEF DESCRIPTION OF THE DRAWINGS

The file of this patent contains at least one drawing executed in color. Copies of this patent with color drawings will be provided by the Patent and Trademark Office upon request and payment of the necessary fee.

FIG. 7A is a three-dimensional color-flow image of rabbit anterior segment derived from sixty-four consecutive scans arranged meridionally at 0.5 degree intervals;

FIG. 7B is a two dimensional section representing a single plane in the three dimensional image shown in FIG. 7A;

FIG. 8A is a view of a magnified region of a superficial vein in an elbow of a normal human subject;

FIG. 8B is a view of the magnified region shown in FIG. 8A in which the phase information has been discarded; and FIG. 8C is a color-flow image of the magnified region derived from signal processing which included alignment of adjacent vectors, wall filtering, and color-flow encoding.

DETAILED DESCRIPTION

Figure 2A:
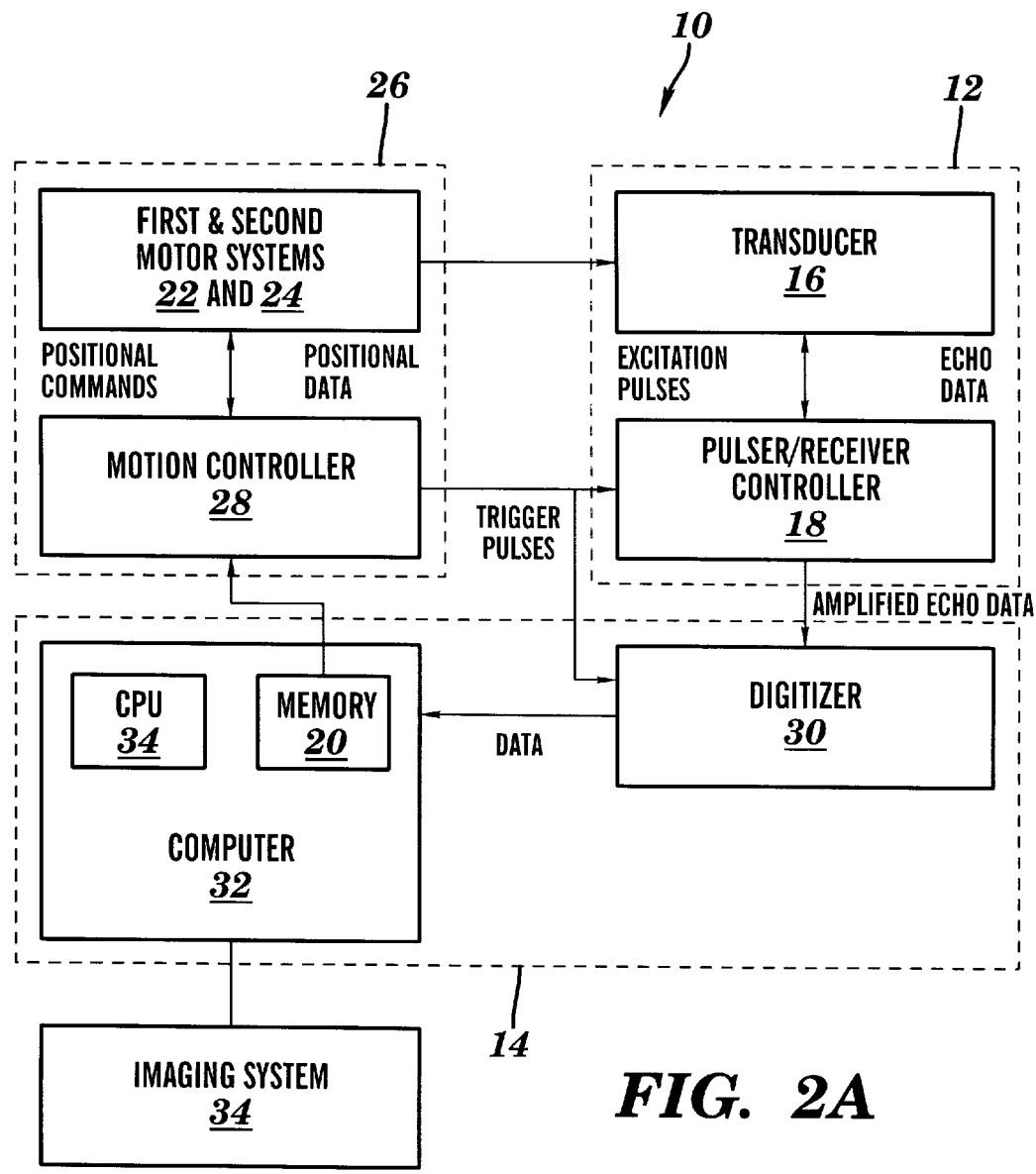
FIG. 2A is a block diagram of an apparatus for assessing blood flow in accordance with one embodiment of the present invention.

An apparatus 10 for assessing blood flow in accordance with one embodiment of the present invention is illustrated in FIG. 2A. The apparatus 10 includes a transmission system 12 and a storage system 14. A method of assessing blood flow in a tissue in accordance with one embodiment of the present invention includes sequentially directing a beam through the tissue along overlapping lines of sight and then generating blood flow data from echo data from where the beams overlap to evaluate the blood flow. This invention includes an apparatus and method for visualizing and measuring blood-flow in different regions of the body at higher resolution and at lower flow rates than conventional Doppler systems. Additionally, the present invention provides an apparatus and a method for assessing blood flow in small vessels, such as those that supply structures in the anterior segment of the eye where the vessels are typically less than 300 microns and the blood velocity may be less than 1.5 cm/sec. Further, unlike prior techniques, the present invention allows a filter to be continuously applied to the return of the ultrasonic beam or pulse from all regions.

In this invention, a technique is described that allows color-flow imaging and measurement of flow rates without sacrifice of resolution. The discussion largely involves use of very high-frequency (50 MHz) ultrasound systems that can provide extremely high spatial resolution. The discussion will also largely involve ophthalmic applications of this system. Ophthalmic applications are of special interest because the eye's peripheral location allows us to use very high frequency ultrasound without the attenuation that would occur if these frequencies were used to image deeper structures. While ophthalmic applications shall be most fully discussed, it should not be construed that the invention is in any way limited to use for diagnosis of ocular disease. Similarly, it should not be construed that the technique is limited to use with very high frequency ultrasound. The method to be described is generally applicable to any ultrasonic frequency range and to any area of the body accessibly to ultrasonic examination.

Figure 2B:
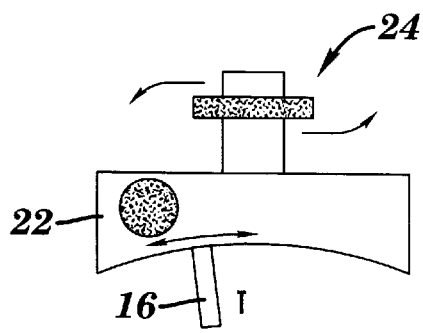
FIG. 2B is a diagram illustrating the operation of the motors and transducer in the embodiment shown in FIG. 2A.

Referring to FIGS. 2A and 2B, the apparatus 10 includes the transmission system 12. In this particular embodiment the transmission system 12 includes a transducer 16 and a pulser/receiver or transducer controller 18, although other types of transmission systems 12 could be used. The pulser/receiver controller 18 is coupled to the transducer 16, to a motion controller 28, and to a digitizer 30. By way of example only, the transducer 16 could be a 50 MHz high frequency polymer transducer, such as Model PI-50 produced by Panametrics Inc. in Waltham, Mass., although other types of transducers could be used. Although in this embodiment, the transducer emits an ultrasonic beam or pulse, other clinically useful ranges of frequencies, such as between about two to fifty MHz, could also be used.

In this particular embodiment, the motion control system 26 includes the first motor system 22, the second motor system 24, and a motion controller 28, although other types of motion control systems 26 can be used. The motion controller 28 is coupled to the first and second motor systems 22 and 24 and to the pulser/receiver controller 18. The first and second motor systems 22 and 24 are connected to the transducer 16. By way of example only, the transducer 16 and first and second motor systems 22 and 24 may be mounted to a fully adjustable tripod (not shown) for easy access to animals or patients lying in the supine position, although other methods of mounting or arranging the transducer 16, first and second motor systems 22 and 24 and other components may also be used. Since the components of and operation of motor systems 22 and 24 to control the motion of an object, such as a transducer 16, are well known to those of ordinary skill in the art, they will not be discussed in detail here. Although two motor systems 22 and 24 are shown, the motion control system 26 could have more than two motor systems or only one motor system and could move the transducer along a variety of different paths. Additionally, although electro mechanical type controls are illustrated in this particular example for the motion control system 26, other types of electronic and/or software controls could also be used to control the direction of transmission of the beam, such as motion controls for the operation of a linear array. By way of example only, first and second motor systems could each be a high speed DC motor that is controlled via a programmable interface, such as model DMC-1000 produced by Galil Motion Control located in Mountain View, Calif., although other types of motor systems could be used.

In this particular embodiment, the storage system 14 includes a processing system or computer 32 and a digitizer 30, although other types of storage systems 14 could be used. The computer 32 includes a central processing unit (CPU) 34, the memory 20, and boards (not shown) for the control of the digitizer, motion controller, and pulser/receiver controller. The computer 20 is coupled to the motion controller 28 and to the digitizer 30 and the digitizer 30 is coupled to the pulser/receiver controller 18. An optional imaging system 34 may be coupled to the computer 32. The imaging system 34 may include a display (not shown) for outputting images of the scanned region. The board for the motion controller 28 controls power amplifiers (not shown) that drive the first and second motor systems 22 and 34 and also controls the positional commands and data which control positioning of the transducer 16. By way of example only, the digitizer board may be an eight bit, one GHz maximum sample rate digitizer card with an 8K buffer, such as model STR81G produced by Sonix, Inc. in Springfield, Va., although other types of boards or controls could be used.

Figure 1A:
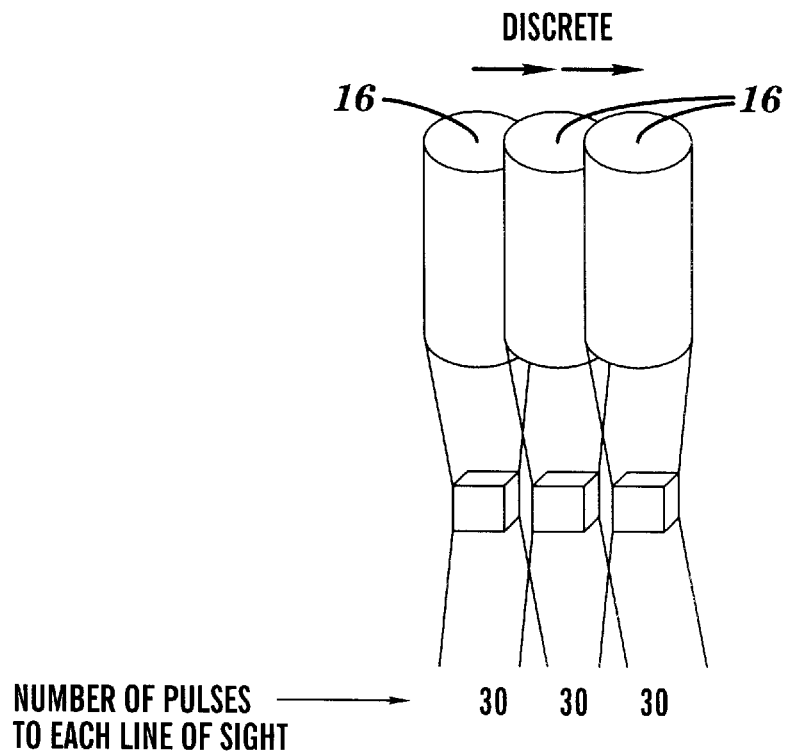
FIG. 1A is a diagram illustrating a discrete lines-of-sight mode for a single element transducer system where the cylinders represent the piston transducer and the cubes represent the focal volumes for each line-of-sight.
Figure 1B:
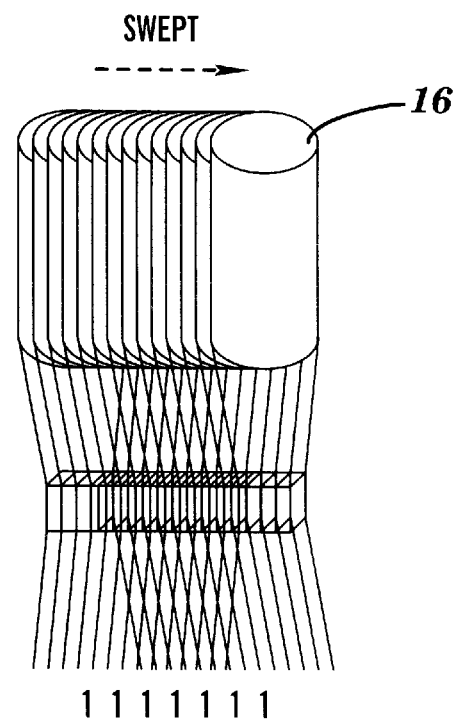
FIG. 1B is a diagram illustrating a swept-scan mode for a single element transducer system where the cylinders represent the piston transducer and the cubes represent the overlapping focal volumes.

The operation of the apparatus in accordance with one embodiment of the present invention will be discussed with reference to FIG. 2A. When the invention is used, the beam needs to be coupled to the region to be examined. For example, if the eye is being examined, the ultrasonic energy will typically be coupled to the eye through a small water bath. To sequentially transmit the beam, in this example, the pulser/receiver controller 18 emits excitation pulses to the transducer 16 in response to one or more trigger pulses. In response to the trigger pulses, the transducer 16 emits a beam or an acoustic pulse. The beam or acoustic pulse is sequentially directed towards the tissue to be evaluated along overlapping lines of sight as shown in FIG. 1B. By way of example only, the transmission system could acquire 1024 lines at 2 $\mu$m spacing by 512 samples in depth at a combined stepping and PRF rate of 500 Hz. Additionally, in this example, each 2-D frame is acquired in approximately two seconds and is quickly transferred to a memory 20 in the storage system 14 for storage and later analysis. In this example, the transducer 16 converts the echo data to voltages and then transmits the voltages to the pulser/receiver controller 18 which amplifies the voltages before storage, although the echo data could be converted in other fashions or simply stored in its current form.

In this example, the motion controller 28 transmits and receives positional commands and data from the first and second motor systems 22 and 24. When the first and second motor systems 22 and 24 receive positional commands, the motor systems 22 and 24 are engaged to move the transducer 16. In this example as shown in FIG. 2B, the first motor system 22 moves the transducer 16 along an arc while the second motor system 24 rotates the transducer 16 to allow for the acquisition of a series of meridional scans at regular fixed intervals. As the transducer 16 moves, the motion controller 28 gets positional feedback data from the first and second motor systems 22 and 24. The motion controller 28 emits the trigger pulses to the pulser/receiver controller 18 at regular intervals in response to positional commands and data as well as instructions from the computer 32.

In this example, the amplified voltages (which represent the converted echo data received by the transmission system 12) are put in digital form by the digitizer 30 and transmitted to the computer 32 for storage and processing, although the digitizing step is optional. The method described herein may be implemented at least partially in software code which is stored in the memory 20 for execution by the central processing unit of the computer 32. Since the components of and operation of computers and software are well known to those of ordinary skill in the art, they will not be discussed in detail here.

The various methods in accordance with the present invention will now be discussed with reference to FIG. 1B and can be carried out by the apparatus illustrated in FIG. 2B. The methods require acquisition of scan vectors at spatial intervals much smaller than the lateral resolution of the transducer 16 at a constant pulse-repetition frequency. The width or lateral resolution of the beam is shown by one face of the cube. If a "resolution cell" is defined to be any group of successive vectors that are within a lateral beam's resolution width of each other, then all vectors within such a cell are highly correlated and may be considered to be interrogating the "same" spatial position. The resultant image represents echo amplitude as a function of range (on the γ-axis) versus lateral position (on the χ-axis), exactly as in a conventional B-mode image. However, because groups of adjacent vectors within the lateral beam width of the transducer are obtained from an overlapping region in space, the local χ-axis can be considered to represent time instead of space (as in an M-scan). Should blood flow exist along a particular line of sight, it appears as an oblique echo trace (range changing with time) within the corresponding resolution cell, whereas stationary structures produce a horizontal trace (range is constant). The axial speed of the flow can easily be determined from the slope of the oblique line (because the local χ- and γ-axes represent time and axial position, respectively). Data acquired using this technique yield a conventional β-scan with embedded time-domain information. Flow rate estimates can be refined by tracing the spatial orientation of a blood vessel in a series of spatially independent resolution cells. By doing so, the angular orientation of the vessel presented to the transducer 16 can be determined and corrected for by using a cosine term.

In human subjects, small saccadic eye movements during scanning are inevitable. The axial component of such movements causes a shift in range of all structures along the given line of sight. One of the advantages of the present invention is that a frame of data can be acquired in about one to two seconds. To improve vascular maps further, flow-induced motion is separated from physiological motion by realigning received signals between adjacent vectors before the estimation of blood velocity. Two correlation-based alignment strategies have been evaluated and their performance described in Zagar, et al., "Ultrasonic Mapping of Microvasculature: Signal Alignment," *Ultrasound Med. Biol. In Press* which is herein incorporated by reference. As disclosed in Ferrara, K. W., et al., "Estimation of Blood Velocity With High Frequency Ultrasound," *IEEE Trans Ultra Freg Cons.*, 43:149–157 (1996), which is herein incorporated by reference, these strategies can compensate for tissue motion in scans of human subjects. Once the vectors are aligned using the strong and spatially uniform tissue echoes, the physiological sources of motion are removed to allow detection of blood flow.

Next, a filter in the computer is used to slowly remove varying tissue echoes, without removing the higher frequency blood echoes. This filter can be implemented using software, hardware, or some combination of both in the computer. In this particular embodiment, a high-pass (wall) filter is used, although other types of filters can be used. An especially useful aspect of this technique relates to the continuously overlapping resolution cells. This facilitates the use of a wall filter to remove clutter (stationary structures) because the filter can be applied in a similarly continuous manner. Because of our overlapping resolution cells, the wall filter continuously processes hundreds, rather than tens, of pulses. The result is that tissue echoes are removed far more effectively than in a conventional Doppler system. This novel result is of particular import for the detection of very low flow velocities.

The velocity of blood flow can then be determined in the computer with an estimation technique, such as the one known as the autocorrelator and disclosed in Kasqi, C., et al., "Real-Time Two-Demensional Blood Flow Imaging Using an Autocorrelation Technique," *IEEE Trans Sonics Ultrason,* SU-32:458–464 (1985) which is herein incorporated by reference. With this technique, velocity resolution is limited, because velocity is estimated based on the change in phase of successive echoes. With the combination of the alignment algorithms, the wall filter, and the autocorrelator in the computer, axial velocities of approximately 0.6 mm/sec can be detected in vessels down to at least 40 μm in diameter. To estimate lower velocities within smaller vessels in the ciliary processes, a higher resolution velocity estimation technique, as disclosed in Ferrara, K., et al., "A New Spread Target Maximum Likelihood Estimator For Blood Velocity Estimation, I: Theory," *IEEE Trans Ultra Ferro Freq Cons.*, 38:1–16 (1991) which is herein incorporated by reference can be used. As discussed earlier, the alignment, filter, autocorrelator, and other steps discussed above can be implemented in software and/or hardware in the computer.

Blood flow can also be evaluated by detecting shifts in echoes generated by moving scatterers relative to stationary reflectors from vector to vector. By measuring the change in range as a function of time (there being a known, fixed time interval between adjacent vectors) the flow rate can be determined. Other techniques for determining blood flow may also be used as needed or desired.

This invention provides several advantages over existing flow measurement systems and signal processing strategies. The center frequency of the transducer 16 is far higher than conventional systems, providing a significant improvement in spatial resolution. Acquisition of a 2-D or 3-D survey of blood flow is made in a "swept mode" in which the transducer 16 is continually moved across the region of interest in an overlapping pattern. This greatly speeds data acquisition and provides the opportunity to use new signal-processing strategies. These strategies include signal alignment to remove physiological motion and a new form of wall filter that eliminates the echoes from tissue. Velocity estimation can then be based on Doppler estimators or time-domain correlation algorithms. The data are well suited for generation of conventional high resolution B-mode images and for simultaneous detection, quantification, and depiction of flow. Small motions of the region being examined can be compensated for by correlation and alignment of adjacent vectors.

Additionally, the method in accordance with the present invention, while retaining the advantages of time-domain techniques, requires far less computational power than does frame-to-frame correlation. Because correlations are between successive vectors within each frame, motion artifacts are also reduced. The continuous nature of the acquisition process and image structure, mixing spatial and temporal dimensions at different scales, make both the acquisition process and wall filtering efficient and uncomplicated. In addition, the method's sensitivity to flow may be enhanced by use of contrast agents.

A number of clinical applications for this invention suggest themselves, including evaluation of diabetic neovascularization of the iris, iris and ciliary body blood flow in glaucoma and hypotony, and evaluation of rumors of the iris and ciliary body. The invention is by no means limited to frequencies in the 50 MHz range and can easily be used with either conventional (10 MHz) or intermediate frequencies, albeit with lower resolution, to assess for example blood flow in more posterior structures of the eye and orbit or other regions of the body. Some of the advantages of the present invention are the relatively high resolution it provides which allows imaging of lower flow rates in smaller vessels and the lower energy emission it provides which may reduce concern regarding temperature increases as compared against prior Doppler systems. This invention also provides a technique for evaluating the effects of glaucoma drug treatments on ocular blood flow. The effects of these drugs on blood flow within the eye are expected to vary greatly, but assessment of their impact has been difficult until the present invention because of the lack of imaging tools with sufficient spatial and velocity resolution. Development of the capability to assess flow quantitatively in each region of the eye could have significant impact on current clinical management and on the integration of the many new glaucoma drugs under development.

Set forth below are some illustrative examples of the method and apparatus in assessing blood flow in tissue:

EXAMPLE 1

Examination of Rabbit Anterior Segment

In this example, the invention was tested by scanning the anterior segment of Dutchbelt rabbit eyes. The rabbits received general anesthesia (35 mg/kg ketamine HCl plus 5 mg/kg xylazine) and the proposed eye was coupled to the transducer with a sterile normal saline water bath. The transducer was placed to position the area of interest in its focal zone. Scans consisting of 1024 vectors were acquired at a pulse-repetition frequency of 500 Hz over an arc of 12° with a radius of curvature of 11 mm. A sample rate of 250 MHz was used, and 512 samples were acquired for each vector. This arrangement produced vectors 2.2 $\mu$m apart, and groups of approximately 30 vectors in each (overlapping) lateral resolution cell. These parameters produced scan planes 2.25 mm wide by 1.5 mm deep in 2 seconds. Consecutive planes were acquired at 0.5° intervals, with the center of each plane displaced 20° from the apex. Adjacent radially offset scan planes had a minimum separation of 35 $\mu$m and a maximum separation of 50 $\mu$m.

Scans were performed as described immediately before topical administration of 2 drops of 1% atropine sulfate. Atropine is classified as an anticholinergic. It causes relaxation of the ciliary muscle and dilation of the pupil. It also acts on the arterioles and thus results in the changes in flow rate. After vessels were identified, M-mode acquisition (pulse-repetition frequency, 500 Hz) was used to evaluate cardiac cycle pulsatility. Swept and M-mode scans were again acquired fifteen minutes after atropine administration.

Figure 3A:
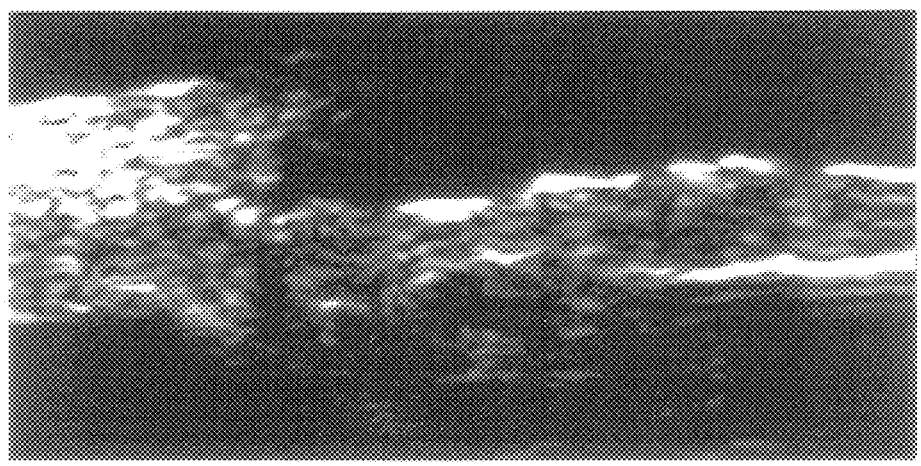
FIG. 3A is a B-mode image of a rabbit eye derived from every eighth vector of 1024 consecutive vectors spaced 2.2 micrometers apart at a rate of 500/sec.
Figure 3B:
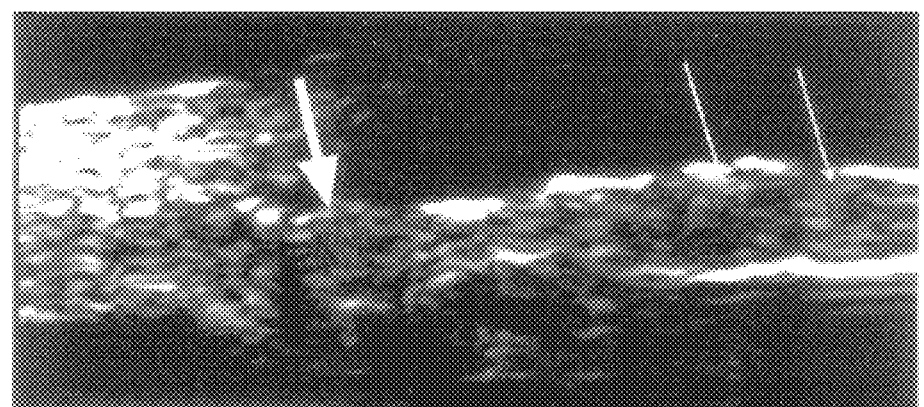
FIG. 3B is the B-mode image of the rabbit eye shown in FIG. 3A derived from all 1024 consecutive vectors.
Figure 3C:
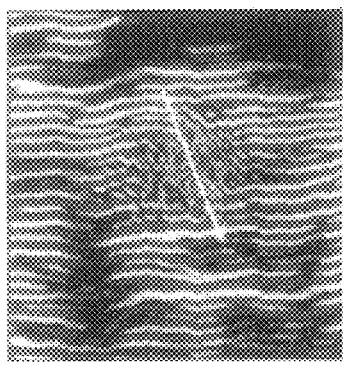
FIG. 3C is a magnified version of a circular, speckle patterned region shown more clearly under the large arrow in FIG. 3B measuring approximately 200 micrometers in diameter.

Referring to FIG. 3A, a B-mode representation of a single-scan plane of the angle is illustrated. In this image, the signal envelope was determined by taking the absolute value of the echo data and averaging. The image in FIG. 3A is reconstructed from every eighth vector—that is, with vectors spaced approximately 18 $\mu$m apart, or approximately four per lateral resolution cell. The image in FIG. 3B is the image shown in FIG. 3A, except that the image has been reconstructed from all 1024 vectors spaced 2.2 $\mu$m apart, or approximately 30 vectors per lateral resolution cell. A comparison of the two images shows no improvement in spatial resolution by oversampling, as would be expected. However, in the highly oversampled image in FIG. 3B, a circular region measuring approximately 200 $\mu$m diameter near the iris root shows a speckle pattern, the slope of which is steep relative to its surround. This is consistent with blood flow. A magnified version of this region in which positive- and negative-phase information are represented in color is illustrated in FIG. 3C. This allows us to track more readily the slope of the flow-induced phase deviation relative to stationary structures. In this case, an uncorrected flow velocity of approximately 3.8 mm/sec was determined.

Figure 4:
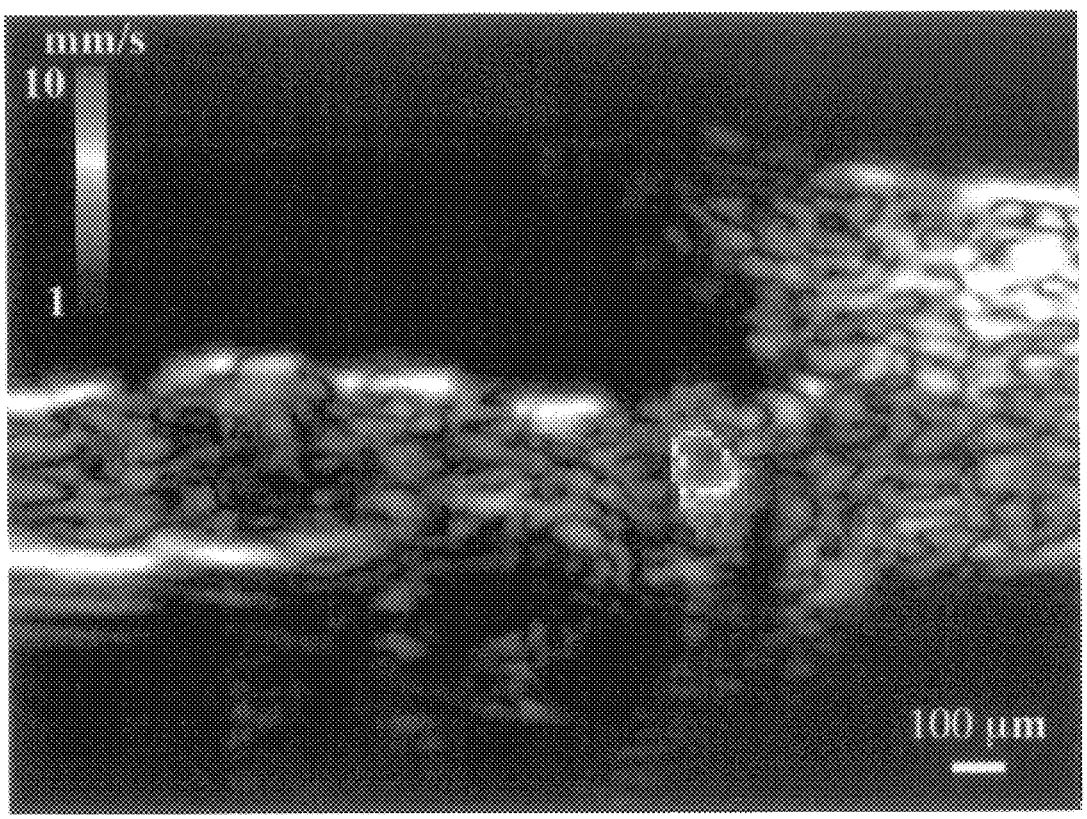
FIG. 4 is a color-flow image illustrating a major arterial circle near the iris root and smaller vessels in the iris in the rabbit eye.
Figure 5:
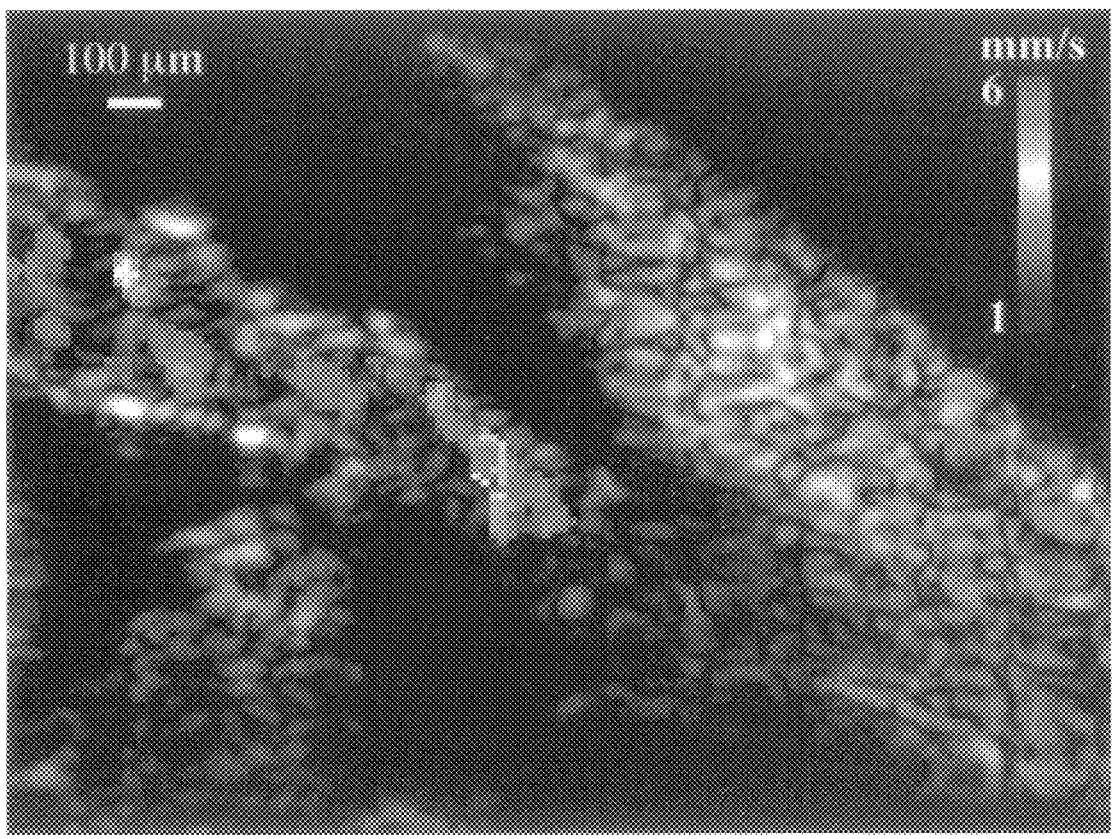
FIG. 5 is a color-flow image illustrating a radial iris in the rabbit eye.

Referring to FIGS. 4 and 5, examples of color-flow images derived from signal processing of echo data for this rabbit's eye are illustrated. In FIG. 4, a color-coded flow in the major arterial circle is visible. In FIG. 5 color flow is evidence in a radial vessel in the iris stroma that, apparently, weaves in and out of the scan plane. Note, however, that the intermittent appearance of the vessel could have been caused by changes in flow rate and echogenicity associated with cardiac cycle, because the 2-second acquisition time encompassed several cycles. Both these factors affect vessel continuity in ultrasound flow images. To evaluate the feasibility of this technique and to provide initial estimates of reliability and sensitivity, sequential sets of flow maps were acquired from a small series of rabbits before and after the application of topical atropine. A substantial variation in flow velocity was recorded between individual rabbits within the series, although repeated evaluation of the same rabbit produced nearly identical results. Thus, velocities recorded from individual rabbits are reported.

Figures 6A, 6B, 6C:
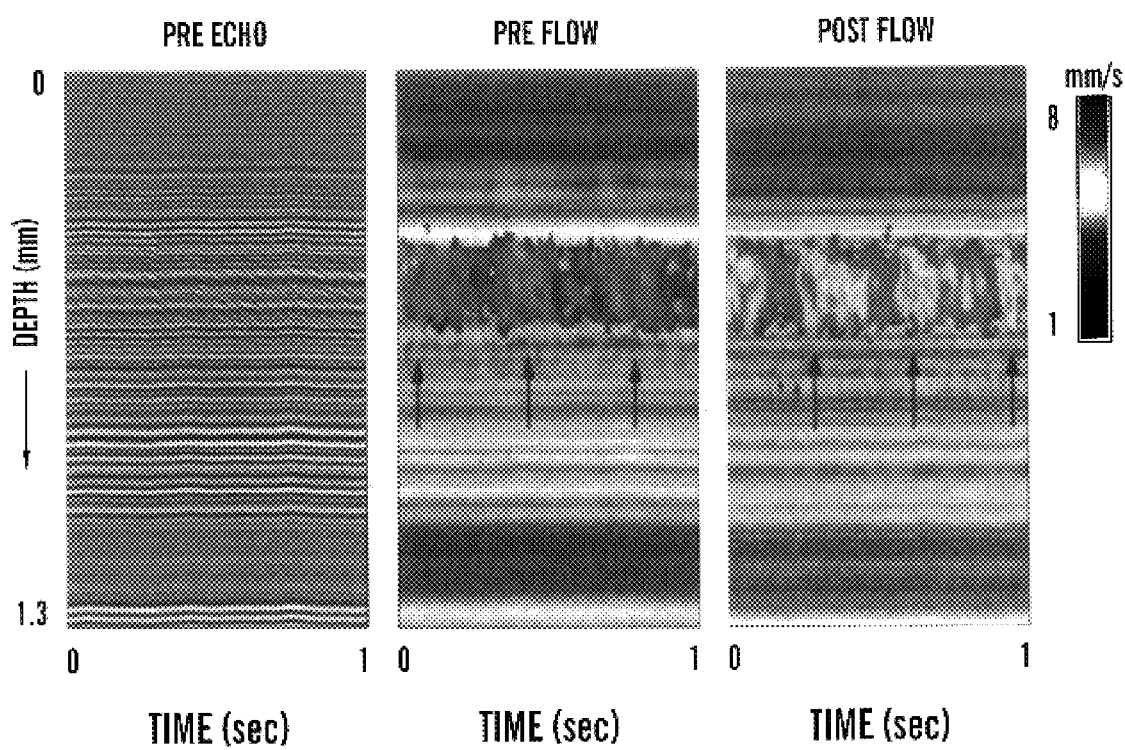
FIGS. 6A–6C are pre-echo, pre-flow, and post flow M-mode images and color maps illustrating cardiac cycle pulsatility.

Evaluating the major arterial circle, the maximum flow velocity and volume flow within the vessel was calculated. An evaluation of the changes in velocity and flow rate was conducted in M-mode and is reported below. From a 2-D image (such as in FIG. 4), a single line of sight within the major arterial circle was interrogated, producing the M-mode image shown in FIGS. 6A–6C. The signal processing techniques described in the previous section were then applied to estimate blood velocity within this region. Resultant maps of blood velocity before and after the application of atropine are shown in FIGS. 6B and 6C, respectively. Note that the effect of cardiac pulsatility is evidence in these figures because of the periodic variation in velocity magnitude shown in the displayed color image.

This example was conducted to evaluate the ability of the invention to monitor changes in blood velocity over the cardiac cycle and measure the effects of vaso-active drugs. It is important to quantify changes occurring over the cardiac cycle to assess the sources of variance in 2-D and 3-D maps of blood flow. From data collected over a sequence of seven cardiac cycles, the angle-corrected spatial and temporal peak velocities in the major arterial circle were found to be 4.57±0.54 mm/sec (SD) and 3.32±0.15 mm/sec during systole and diastole, respectively. Thus, the variation in peak velocity estimated over the cardiac cycle was 27% of peak systolic velocity.

After the application of atropine, the angle-corrected spatial and temporal (systolic) peak velocity in the major arterial circle was 7.88±0.49 mm/sec. The spatial peak velocity during diastole was 4.85±0.44 mm/sec. Thus, the variation in velocity estimated over the cardiac cycle after the application of atropine was 38% of the peak systolic velocity. The 72% increase in peak systolic velocity and 46% increase in diastolic velocity after atropine administration were clearly detectable with this technique (P<0.01). Thus, single line-of-sight M-mode evaluation provided a tool to evaluate pulsatic flow within small blood vessels and the effect of vasoactive therapies.

Next, the variation of maximum velocity ($V_{max}$) and volume flow in a single 2-D frame was estimated. To determine the variance in velocity estimates, 2-D frames from a single spatial region were acquired before and after application of topical atropine. Because each 2-D frame was acquired in approximately two seconds, individual frames contained echoes acquired from cardiac systole and diastole. The resultant variation in peak velocity between successive 2-D frames was 34% of its peak value and therefore was a magnitude similar to the fluctuations over the cardiac cycle recorded in M-mode, as described earlier. The vessel area could also be estimated from the 2-D view to produce a volume flow rate. The estimated volume flow rate based on the average velocity for this vessel was 0.13±0.04 $\mu$l/sec.

After the application of atropine, the spatial $V_{max}$ was recorded and averaged over a sequence of six frames. The increase in spatial $V_{max}$ produced by atropine in the 2-D frames was 54%, between the estimates of 72% for systole and 46% for diastole made in M-mode. This is expected because each 2-D frame contains echoes acquired during systole and diastole.

A 3-D volume rendered model from a group of 64 sequential scan planes was produced. In FIG. 7A, after reducing the opacity of stationary structure, color-coded flow in the major arterial circle is evidence, with a peak velocity of 1.6 cm/sec. A small branch from this circle can be visualized entering the ciliary body. Visualization of flow and vessel diameter in the small branches from the major arterial circle is particularly important for the assessment of vasoactive drugs used to treat glaucoma. A 2-D slice from this 3-D volume is then presented in FIG. 7B to aid in visualization of the anatomy. These 3-D reconstructions of the vascular architecture provide the opportunity to determine the angle between the ultrasound beam and each vessel, allowing computation of angle-corrected flow velocity. Anatomy, however, is more easily recognized in 2-D planes that can be derived from the 3-D data.

EXAMPLE 2

Examination of a Superficial Vessel in an Elbow of a Human Subject

A color image relating to the use of our ultrasound blood-flow technique in accordance with one embodiment of the present invention is illustrated in FIGS. 8A–8C. The image is of a superficial vein in the elbow of a normal subject. In this case, a lower frequency transducer was used than in the above example on very high frequency (50 MHz) imaging of flow in the ciliary body and iris of the rabbit eye. In this example, data was acquired using a 15 MHz transducer. The scan consisted of 512 vectors of 2048 bytes each. A pulse repetition frequency of 500 Hz was used, with a resultant 1 second acquisition time. Vectors were spaced 10 microns apart, producing a 5 mm wide scan. A 100 MHz sample rate was used, producing a scan depth of ~12.5 mm.

The image in FIG. 8A shows a magnified region in the scan data corresponding to the vein. The data are presented as a raw 'phase' image, in which positive and negative magnitude are represented in blue and red, facilitating tracking of flow. The horizontal axis represents both lateral position (on large scales) and time (on smaller scales approximately 30 adjacent vectors). The vertical axis represents depth. Thus, flow results in diagonal phase contours, which are very evident. The image in FIG. 8B represents the envelope of the data in which phase information has been discarded. The image in FIG. 8C is a color-flow image derived from signal processing (alignment of adjacent vectors, wall filtering and color-flow encoding) of the data.

This example demonstrates the use of our method at lower frequencies which are suitable for imaging of deeper structures (carotid arteries, breast, abdominal, ob-gyn, etc.). This technique will allow improved resolution and (possibly) lower power levels than current Doppler technology.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Accordingly, the invention is limited only by the following claims and equivalents thereto.

What is claimed is:

1. A method of assessing blood flow in a tissue comprising:

sequentially directing a beam through the tissue along generally parallel, overlapping lines of sight in a focal region; and generating blood flow data from echo data from reflections of the sequentially directed beams from where the beams overlap to evaluate the blood flow in the tissue.

2. The method according to claim 1 wherein the beam is an ultrasonic beam.

3. The method according to claim 1 wherein the beam has a lateral resolution and the lines of sight are spaced apart at intervals which are smaller than the lateral resolution of the beam.

4. The method according to claim 1 wherein the tissue is a blood vessel smaller than 300 microns.

5. The method according to claim 1 further comprising obtaining the generated blood flow data in less than two seconds.

6. The method according to claim 1 further comprising determining blood flow velocity in the tissue based on the blood flow data.

7. The method according to claim 6 wherein the step of determining blood flow velocity comprises:

demodulating the blood flow data to remove a carrier frequency; and estimating the blood flow velocity from the demodulated blood flow data.

8. The method according to claim 7 wherein the step of demodulating comprises using quadrature amplitude demodulation.

9. The method according to claim 6 wherein the step of determining blood flow velocity comprises:

aligning the blood flow data to remove physiological sources of motion; and estimating the blood flow velocity from the aligned blood flow data.

10. The method according to claim 9 wherein the step of aligning comprises using an incremental alignment procedure.

11. The method according to claim 6 wherein the step of determining blood flow velocity comprises:

filtering the blood flow data to remove tissue motion; and estimating the blood flow velocity from the filtered blood flow data.

12. The method according to claim 11 wherein the filtering is applied continuously.

13. The method according to claim 11 wherein the step of filtering comprises using a wall filter.

14. The method according to claim 6 further comprising applying thresholds to the determined blood flow velocity to remove noise.

15. The method according to claim 1 further comprising providing an image of the blood vessel in the tissue based on the blood flow data.

16. A method of measuring blood flow velocity in at least one vessel in a tissue comprising:

sequentially directing a beam through the vessel in the tissue along generally parallel, overlapping lines of sight in a focal region;

generating the blood flow data from echo data from reflections of the sequentially directed beams from where the beams overlap; and determining the blood flow velocity in the vessel from the generated blood flow data.

17. The method according to claim 16 wherein the beam is an ultrasonic beam.

18. The method according to claim 16 wherein the beam has a lateral resolution and the lines of sight are spaced apart at intervals which are smaller than the lateral resolution of the beam.

19. The method according to claim 16 wherein in the tissue is a blood vessel smaller than 300 microns.

20. The method according to claim 16 further comprising obtaining the generated blood flow data in less than two seconds.

21. The method according to claim 16 wherein the step of determining blood flow velocity comprises:

demodulating the blood flow data to remove a carrier frequency;

aligning the blood flow data to remove physiological sources of motion;

filtering the blood flow data to remove tissue motion;

estimating the blood flow velocity from the demodulated, aligned, and filtered blood data.

22. The method according to claim 21 wherein the step of demodulating comprises using quadrature amplitude demodulation.

23. The method according to claim 21 wherein the step of aligning comprises using an incremental alignment procedure.

24. The method according to claim 21 wherein the filtering is applied continuously.

25. The method according to claim 21 wherein the step of filtering comprises using a wall filter.

26. The method according to claim 21 further comprising applying thresholds to the estimated blood flow velocity to remove noise.

27. A method of analyzing a vessel in a tissue comprising:

sequentially directing a beam through the vessel in the tissue along generally parallel, overlapping lines of sight in a focal region;

generating blood flow data from echo data from reflections of the sequentially directed beams from where the beams overlap; and providing an image of the vessel from the generated blood flow data.

28. The method according to claim 27 wherein the beam is an ultrasonic beam.

29. The method according to claim 27 wherein the beam has a lateral resolution and the lines of sight are spaced apart at intervals which are smaller than the lateral resolution of the beam.

30. The method according to claim 27 wherein the vessel is smaller than 300 microns.

31. The method according to claim 27 further comprising obtaining the generated blood flow data in less than two seconds.

32. An apparatus for assessing blood flow in a tissue comprising:

a transmission system that sequentially transmits a beam towards the tissue along a plurality of generally parallel, overlapping lines of sight in a focal region and receives echo data from reflections of the sequentially directed beams from the transmission along each of the lines of sight; and a storage system storing the echo data.

33. The apparatus according to claim 32 wherein the beam is an ultrasonic beam.

34. The apparatus according to claim 32 wherein the beam has a lateral resolution and the lines of sight are spaced apart at intervals which are smaller than the lateral resolution of the beam.

35. The apparatus according to claim 32 wherein the transmission system comprises:

a linear array; and an array controller coupled to the linear array, wherein the array controller transmits an excitation pulse to the linear array in response to a trigger pulse and the linear array transmits the beam in response to the excitation pulse.

36. The apparatus according to claim 32 wherein the transmission system comprises:

a transducer; and a transducer controller coupled to the transducer, wherein the transducer controller transmits an excitation pulse to the transducer in response to a trigger pulse and the transducer transmits the beam in response to the excitation pulse.

37. The apparatus according to claim 36 further comprising a motion control system connected to the transducer and transducer controller, the motion control system moving the transducer so that the beam is transmitted along the overlapping lines of sight.

38. The apparatus according to claim 36 wherein the motion control system comprises:

at least one motor system coupled to the transducer; and a motion controller coupled to the motor systems which controls the operation of the motor systems and transmits the trigger pulses to the transducer controller.

39. The apparatus according to claim 38 wherein the storage system comprises a processing system with a memory coupled to the motion control system and the transmission system, the processing system storing the echo data and controlling the operation of the motion control system and the transmission system.

40. The apparatus according to claim 39 further comprising a digitizer coupled between the processing system and the transducer controller which puts the echo data in digital form.

41. The apparatus according to claim 40 wherein the filter is applied continuously.

42. The apparatus according to claim 40 wherein the filter is a wall filter.

43. The apparatus according to claim 36 wherein the motion control system further comprises another motor system connected to the transducer and coupled to the motion controller.

44. The apparatus according to claim 32 wherein the storage system comprises a processing system, the processing system determining blood flow velocity in the tissue based on the echo data.

45. The apparatus according to claim 44 wherein the processing system further comprises a demodulator which removes a carrier frequency from the echo data.

46. The apparatus according to claim 45 wherein the processing system further comprises a filter which removes tissue motion from the echo data.

47. The apparatus according to claim 32 further comprising providing an imaging system, the imaging system providing an image of blood flow in the tissue based on the echo data.

* * * * *